United States Patent [19]

Imran

[11] Patent Number: 5,947,985

[45] Date of Patent: Sep. 7, 1999

[54] APPARATUS AND METHOD FOR CLEANING DISEASED VEIN GRAFTS

[76] Inventor: Mir A. Imran, 26641 Laurel La., Los Altos Hills, Calif. 94025

[21] Appl. No.: 08/968,146

[22] Filed: Nov. 12, 1997

[51] Int. Cl.[6] .................................................. A61B 17/22
[52] U.S. Cl. .......................... 606/159; 606/170; 606/113; 606/200; 604/22; 604/43; 604/101; 604/102
[58] Field of Search ..................................... 606/159, 170, 606/113, 200; 604/101, 102, 22, 43

[56] References Cited

U.S. PATENT DOCUMENTS

| | | | |
|---|---|---|---|
| 4,706,671 | 11/1987 | Weinrib | 606/159 |
| 5,255,679 | 10/1993 | Imran | 128/642 |
| 5,462,529 | 10/1995 | Simpson et al. | 604/101 |
| 5,702,413 | 12/1997 | Lafontaine | 606/159 |
| 5,728,123 | 3/1998 | Lemelson et al. | 606/159 |
| 5,782,848 | 7/1998 | Kennox | 606/159 |

*Primary Examiner*—Michael Buiz
*Assistant Examiner*—Lien Ngo
*Attorney, Agent, or Firm*—Flehr Hohbach Test Albritton & Herbert LLP

[57] ABSTRACT

Apparatus for cleaning a vessel having a stenosis therein comprising first and second balloon catheters. Balloons are disposed on opposite sides of the stenosis in the vessel and form a closed chamber in the vessel. A therapeutic catheter having a distal extremity is disposed in the chamber. Irrigation liquid is supplied to the chamber and liquid is aspirated from the chamber to form an aspirate. The distal extremity of the therapeutic catheter is moved to cause the material forming the stenosis to be removed from the wall of the vessel and to be broken into particles which are removed with the aspirate.

6 Claims, 2 Drawing Sheets

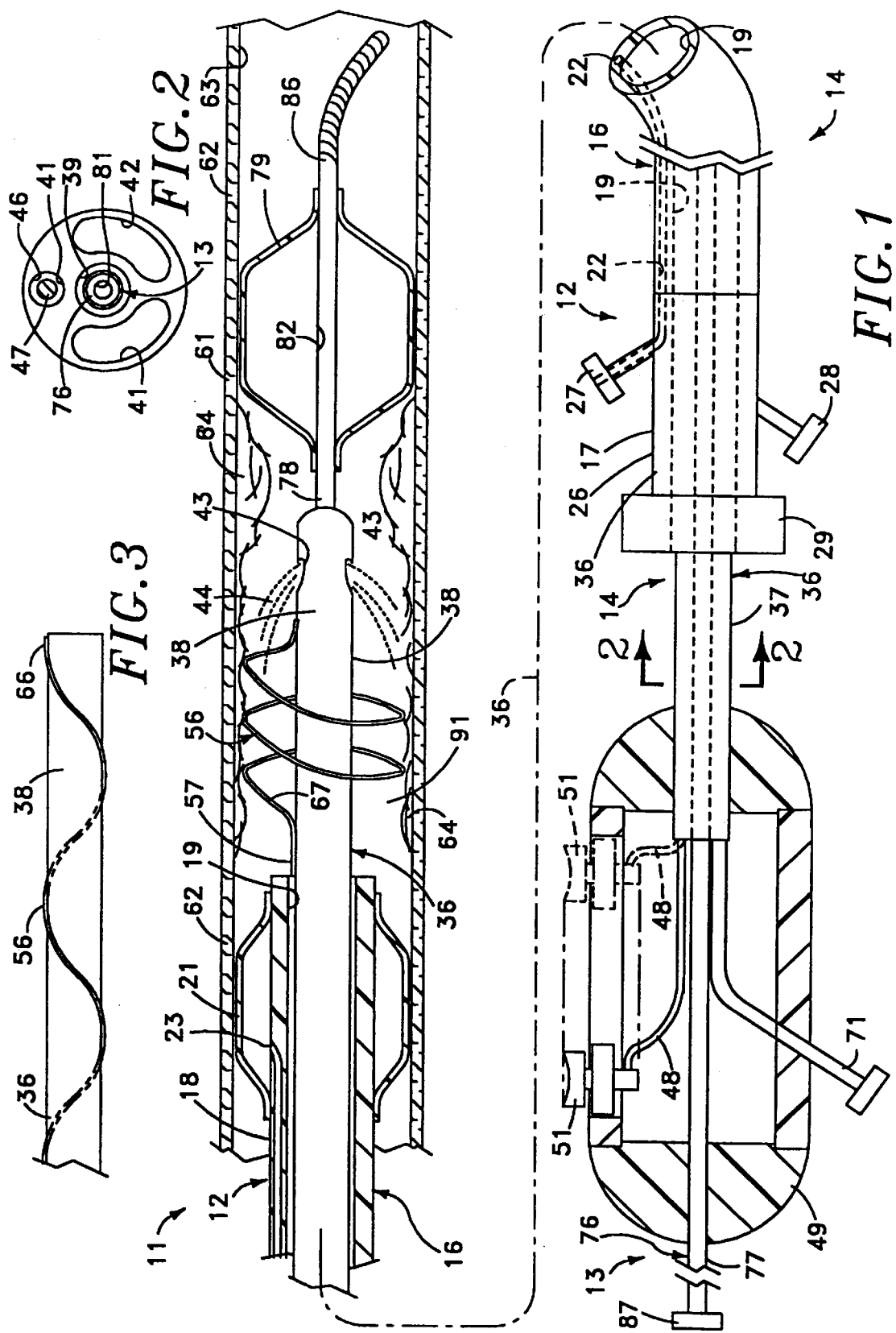

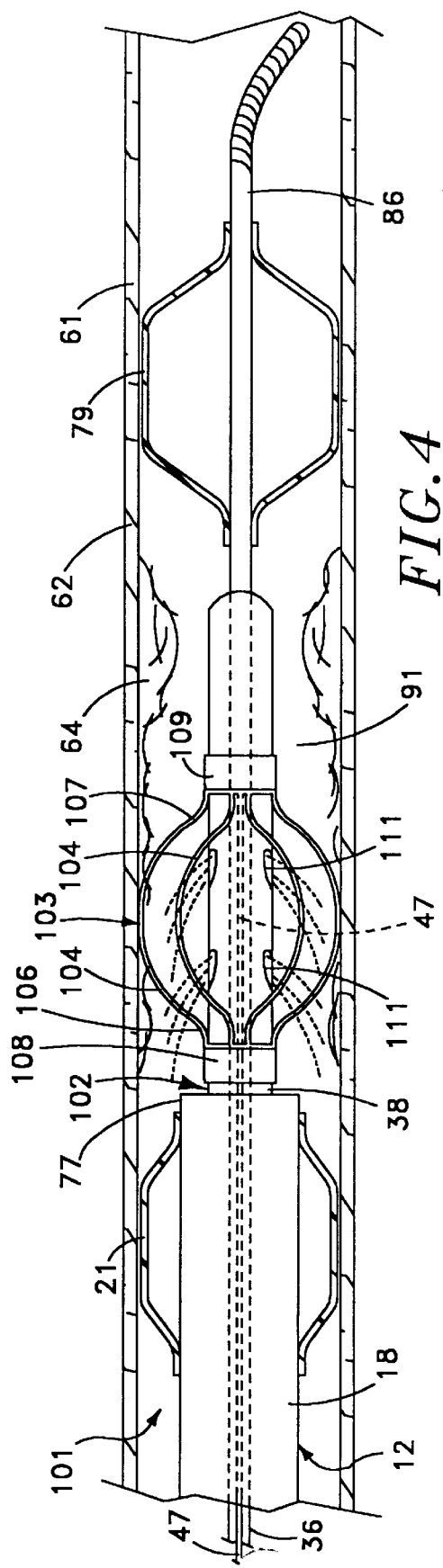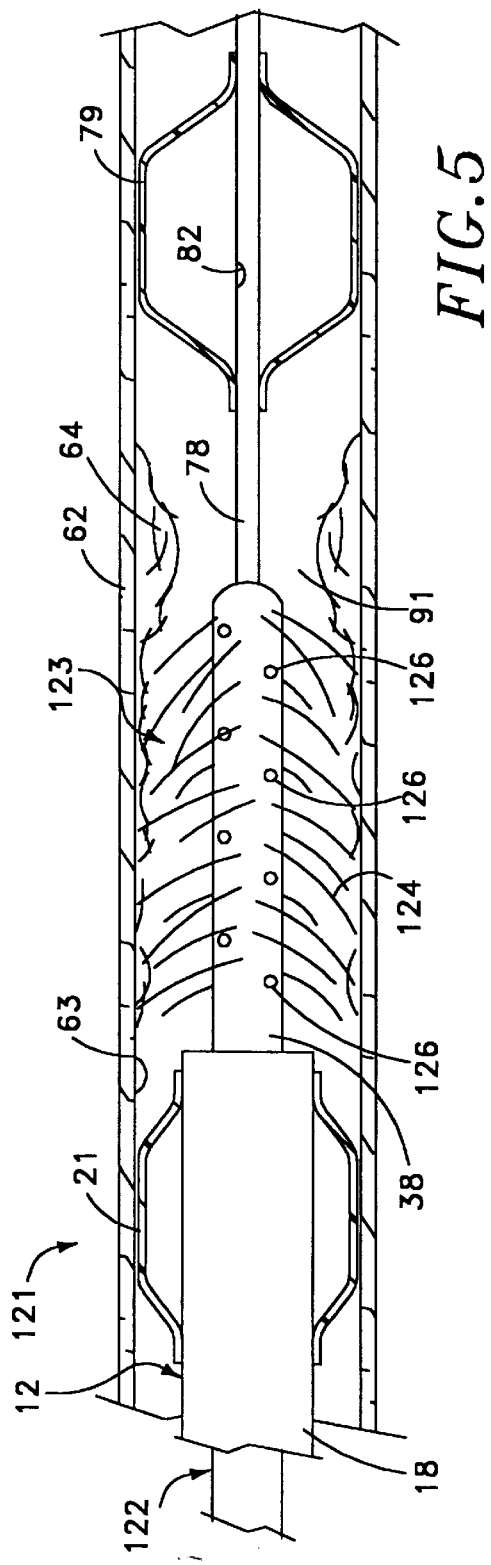

APPARATUS AND METHOD FOR CLEANING DISEASED VEIN GRAFTS

This invention relates to an apparatus and method for cleaning diseased vein grafts and other vessels in which the plaque forming the stenosis therein is relatively soft.

During bypass surgery in replacing diseased vessels in the heart, it is conventional to utilize the saphenous veins in the body of the same person and utilizing portions of those veins to create bypass grafts in diseased vessels in the heart. However, it has been found that such vein grafts have a tendency to clog up within a period of time with the average being approximately eight years. It has been found that this clogging of the veins occurs by a very different process from the arterial atherosclerotic disease typically found in the coronary arteries in the carotids and other blood vessels in the body. Because the saphenous vein graft during the bypass procedure is expanded and reimplanted, much of the vessel becomes fibrose and dies. For this reason it does not have the cholesterol based lesion that typically forms underneath the intima of coronary arteries and other healthy vessels. Rather it has been found that within the implanted saphenous vein grafts, a layer of lipids and other material lie in the inner surface of the graft. This layer of lipids forms an atheroma which usually builds up. Also, there is typically formed a thrombus which leads to a severe constriction in the graft and ultimately complete closure. This leads to angina and other symptoms necessitating treatment of this condition. In the past the procedure has been to perform another bypass procedure utilizing a saphenous vein graft from the other leg of the patient. Alternatively, a balloon angioplasty procedure including stenting is used. However, this latter procedure is particularly dangerous because of the softness of the material within the vein graft which makes it easy to dislodge and create embolic events downstream of the graft. The incidence of such embolic events has been recorded to be as high as 40% and often at least as high as 20%. There is therefore need for a new and improved graft and method which makes it possible to clean or clear the vein graft while limiting the exposure of the patient to embolic events.

In general, it is an object of the present invention to provide an apparatus and method for cleaning diseased vein grafts and other vessels in the body including soft substances therein which create stenoses in the vessel.

Another object of the invention is to provide an apparatus and method of the above character which makes it possible to avoid embolitic events downstream of the graft.

Another object of the invention is to provide an apparatus and method of the above character which makes possible cleaning of the vessel without damage to the vessel.

Additional objects and features of the invention will appear from the following description which preferred embodiments are set forth in detail in conjunction with the accompanying drawings.

FIG. 1 is a side-elevational view partially in cross section of an apparatus incorporating the present invention for cleaning vein grafts and particularly saphenous vein grafts.

FIG. 2 is a cross-sectional view taken along the line 2—2 of FIG. 1.

FIG. 3 is a side-elevational view of the distal portion of the therapeutic catheter shown in FIG. 1 with the helix provided thereon in a contracted position.

FIG. 4 is a side-elevational view partially in section of apparatus incorporating another embodiment of the present invention for cleaning diseased vein grafts.

FIG. 5 is another partial side-elevational view partially in section of another embodiment of the apparatus incorporating the present invention for cleaning diseased vein grafts.

In general, the apparatus of the present invention for cleaning a vessel with a stenosis therein comprises first and second balloon catheters having balloons disposed on opposite sides of the stenosis in the vessel and forming a closed chamber in the vessel. A therapeutic catheter is provided which has a distal extremity disposed in the chamber. Means is provided for supplying an irrigation liquid to the chamber. Means is also provided for aspirating liquid from the same chamber. Means is provided for causing movement of the distal extremity of the therapeutic catheter to cause material to be removed from the wall of the vessel and thereafter to be removed from the vessel along with the aspirating liquid.

More in particular as shown in FIGS. 1, 2 and 3 of the drawings, the apparatus 11 for cleaning vein grafts consists of a main occlusion balloon catheter 12, a distal occlusion balloon catheter 13 and a therapeutic catheter 14. The main occlusion balloon catheter 12 consists of a flexible elongate tubular member 16 having proximal and distal extremities 17 and 18. It is provided with lumen 19 which extends from the proximal extremity 17 to the distal extremity 18 and opens through the distal extremity 18. An inflatable balloon 21 is mounted on the distal extremity 18. The balloon 21 can be formed integral with the flexible elongate tubular member 16 or can be formed as a separate balloon as shown and secured to the distal extremity by an adhesive (not shown). A balloon inflation lumen 22 is provided in the flexible elongate tubular member 16 and is in communication with the interior of the balloon 21 through a port 23. A fitting 26 is mounted on the proximal extremity 17 of the flexible elongate tubular member 16 and is provided with a balloon inflation side port 27 in communication with the balloon inflation lumen 22. The fitting 26 is also provided with another side port 28 which serves as an aspiration port and which is in communication with the lumen 19. The fitting 26 is also provided with a main port 29 which is in communication with the main lumen 19 and is provided with hemostosis valve means for forming a liquid sealing engagement with the therapeutic catheter 14.

The therapeutic catheter 14 consists of a flexible elongate member 36 which is provided with proximal and distal extremities 37 and 38. It is provided with a central lumen 39 which receives the distal occlusion balloon catheter 13. It also is provided with first and second irrigation lumens 41 and 42 which open through a plurality of irrigation ports 43 provided in the distal extremity 38 adjacent the end of the flexible elongate member 36. The ports 43 which are in communication with the lumens 41 and 42 are formed in such a manner so that irrigation liquids passing therefrom jet proximally or rearwardly to form angularly disposed jets 44 as shown in FIG. 1.

The flexible elongate member 36 is also provided with a pull wire lumen 46 through which a pull wire 47 extends. The pull wire 47 can be formed of a suitable material such as stainless steel and has a proximal extremity 48 which extends into a handle 49 mounted on the proximal extremity 37 of the flexible elongate member 36. The handle 49 carries a slider 51 which is slidably mounted near the proximal end of the handle as shown in FIG. 1 and is connected to the proximal extremity 48 of the pull wire 47. The handle 49 is sized so that it is adaptably gripped by the human hand while permitting a thumb of the same hand to engage the slider 51 to cause movement of the pull wire 47 to thereby cause expansion and contraction of a helix or helical coil 56 secured to the distal extremity 57 of the pull wire 47. The helix or helical coil 56 is formed of a suitable material such as stainless steel or of a suitable shape memory alloy. If formed of a shape memory alloy, it has a preprogrammed shape in the form of an expanded helix which has an outer diameter which corresponds generally to the inner diameter of a vessel 61 such as a saphenous vein graft having a cylindrical wall 62 defining a lumen 63.

Plaque 64 is shown in FIG. 1 formed on the wall 62 which is desired to be removed by the apparatus 11. The helix or helical coil 56 is adapted to be moved between expanded and contracted positions by movement of the pull wire 47 backwards and forwards under the control of the slider 51. Thus when it is pulled rearwardly, the helix 56 is tightly wound onto the outer surface of the distal extremity of the flexible elongate tubular member as shown in FIG. 3 with the distal extremity 66 of the helix being secured to the distal extremity of the flexible elongate member 36 and the proximal extremity 67 being secured to the distal extremity 57 of the pull wire 47 as hereinbefore explained. Irrigation lumens 41 and 42 are in communication with an irrigation port 71 provided on the handle 49.

The distal occlusion balloon catheter 13 as hereinbefore explained is mounted within the main lumen 39 of the therapeutic catheter 14. It consists of a flexible elongate tubular member 76 having proximal and distal extremities 77 and 78. An inflatable balloon 79 is mounted on the distal extremity 78 and can be formed integral with the flexible elongate tubular member 76 or alternatively as shown can be formed as a separate balloon adhered to the distal extremity 78 by an adhesive (not shown). The flexible elongate tubular member 76 is provided with a balloon inflation lumen 81 which extends from the proximal extremity to the distal extremity and is in communication with the interior of the balloon 79 through a port 82 for inflating and deflating the balloon 79. A fixed guide wire 86 is mounted on the distal extremity 77 of the flexible elongate member 76. It should be appreciated that if desired, a movable guide wire can be provided with the distal occlusion balloon catheter 13. It is merely necessary to provide an additional guide wire lumen through which the guide wire can extend through the flexible elongate tubular member 76. A fitting 87 is mounted on the proximal extremity 77 of the flexible elongate tubular member 76 and is in communication with the balloon inflation lumen 81 and is used for inflating and deflating the balloon 79.

Operation and use of the apparatus 11 may now be briefly described as follows. Let it be assumed that saphenous vein graft previously placed in a human patient has been substantially occluded by a stenosis and it is necessary to treat the same. Such a procedure can be accomplished by forming a puncture to open up the femoral artery after which an introducer (not shown) is inserted.

The three catheters forming part of the apparatus can be preassembled by placing the distal extremity of the therapeutic catheter 14 into the main lumen 19 with the helix or helical coil 56 in a contracted position disposed within the distal extremity of the flexible elongate member 16. This assembly of the therapeutic catheter 14 in the main catheter 12 can then be advanced over the distal occlusion balloon catheter 13 until the distal extremity of the main catheter 12 is disposed in close proximity to the distal extremity of the distal occlusion balloon catheter 13. The entire assembly of the apparatus 11 can then be advanced through the introducer and into the arterial vessel utilizing the fixed guide wire 86 to navigate the vessel to bring the entire assembly to the desired position in which the balloons 79 and 62 are disposed on opposite sides of the plaque 64 it is desired to remove. The distal balloon 79 is first inflated to stop the flow of blood through the vessel 63. This is followed by inflation of the proximal balloon 21 so that there is formed a closed chamber 91 between the same. As soon as the closed chamber 91 has been formed, the therapeutic catheter 14 can be moved relative to the main occlusion balloon catheter 12 to cause the helix to be moved out of the main catheter and into the chamber 91. Irrigation liquid is then supplied through the irrigation port 71. The aspiration port 28 is connected to a suitable vacuum source for aspirating the irrigation liquid introduced into the chamber 91 to form an aspirate. As this is occurring, the pull wire 47 can be operated by pushing the slider 51 forwardly to cause the helix 56 to expand to its normally expanded position and into yieldable spring-like engagement with the wall 62 defining the lumen 63 of the vessel 61. With the helix 56 in this position, the therapeutic catheter 14 can be moved backwards and forwards within the confines of the chamber 91 by use of the handle 49 grasped by the physician performing the procedure. The soft material forming the plaque 64 is quickly removed by this procedure and broken up into particles which can be readily removed with the aspirate through the aspiration port 28. By repeatedly moving the helix 56 back and forth within the vessel 61, it is possible to completely clean the plaque from the wall 61. Typically this can be accomplished in a relatively short period of time, for example within a period of 10–15 seconds without causing damage to the heart muscle.

After this back and forth movement has been completed, the helix 56 can again be brought back to its contracted position by pulling on the slider 51 to pull the pull wire 47 rearwardly to collapse the helix around the distal extremity of the flexible elongate tubular member 36 shown in FIG. 3. The therapeutic catheter 14 can then be withdrawn so that the distal extremity is brought into the open end of the distal extremity 18 of the flexible elongate tubular member 16 of the main occlusion balloon catheter 12. The supply of liquid to the irrigation jets or openings 43 is then terminated. Aspiration also can be terminated at this time after which the balloon 21 can be deflated followed by deflation of the balloon 79. The entire assembly 11 can then be withdrawn from the patient and the puncture closed to complete the procedure.

Alternatively rather than introducing an assembly catheters at the same time, the catheters can be introduced individually. Thus, the distal occlusion balloon catheter 13 can be first advanced into the vessel so that the balloon 79 carried thereby is disposed distal of the plaque to be removed. Thereafter, the main occlusion balloon catheter 12 can be advanced over the distal occlusion balloon catheter 13 until its balloon 21 is just proximal of the plaque to be removed. Thereafter, the therapeutic catheter 14 can be introduced over the distal occlusion balloon catheter 13 and through the main occlusion balloon catheter 12 until the distal extremity with the helix 56 thereon has been advanced so that it is adjacent the distal extremity 18 of the flexible elongate tubular member 16 of the main occlusion balloon catheter 12. Thereafter, the balloon 79 can be inflated followed by inflation of the balloon 21 to form the chamber 91 in the manner hereinbefore described. Thereafter, the cleaning operation can be performed by advancement of the therapeutic catheter 14 so that the helix 56 is moved into the chamber and thereafter expanded and pulled back and forth to perform the cleaning procedure. Irrigation liquid can be introduced through the port 71 and aspirate withdrawn from the port 28 carrying with it the particles which are removed from the plaque on the wall in the manner hereinbefore described. After the cleaning operation has been completed, the slider 51 can be retracted to bring the helix into close engagement with the distal extremity of the flexible elongate tubular member 36 of the therapeutic catheter 14. The therapeutic catheter 14 can then be withdrawn into the main occlusion balloon catheter 12. The supply of irrigation liquid through the irrigation port 71 can be discontinued as well as the aspiration from the aspiration port 28. The balloons 79 and 21 can be deflated and thereafter the entire assembly can be withdrawn and the puncture site sealed as hereinbefore described.

An alternative embodiment of the apparatus for performing the cleaning operation is shown in FIG. 4. The apparatus 101 shown therein consists of a main occlusion balloon catheter 12 and a distal occlusion balloon catheter 13 which may be identical to those hereinbefore described. A modified therapeutic catheter 102 is provided in which the helix 56 on the therapeutic catheter 14 has been replaced by a basket-like structure 103 mounted on the distal extremity of the flexible elongate tubular member 36. The basket-like structure 103 is provided with a plurality of circumferentially spaced apart longitudinally extending spring-like arms 104 formed of a suitable material such as stainless steel or preferably of a shape memory alloy. The arms 104 have proximal and distal extremities 106 and 107. The proximal extremities 106 are secured by a fixed collar 108 secured to the distal extremity 38 of flexible elongate tubular member 36 by a suitable means such as an adhesive. The distal extremities 107 of the arms 104 are secured to another collar 109 which is slidably mounted on the distal extremity 38 of the flexible elongate tubular member 36. The movable collar 109 is secured to the distal extremity of the pull wire 47 so that when the slider 51 is advanced, the arms 104 are straightened so they lie in close proximity to the outer surface of the flexible elongate tubular member 36. Conversely, when the pull wire 47 is pulled proximally or rearwardly, the collar 109 is moved rearwardly to cause the arms 104 to be pulled outwardly and to yieldably engage the wall 62 defining the lumen 63. If the arms 104 are formed of a shape memory material, the arms will spring outwardly into the predetermined shape memory provided in the arms when the arms clear the distal extremity 57 of the main catheter 12.

Assuming that the apparatus 101 has been deployed in the manner similar to that hereinbefore described with the balloons 79 and 21 inflated and with an irrigation liquid being supplied to the therapeutic catheter and catheter 102 and exiting through two sets of ports 111 in the flexible elongate tubular member 36 intermediate the proximal and distal extremity of the arms 104. With the arms 104 in an expanded position, the therapeutic catheter 102 can be rotated from the proximal extremities to cause the arms 104 to remove the plaque 64 from the wall 62. At the same time or thereafter, the basket-like structure 103 can be moved forward and then back until the entire interior surface area of the wall 62 has been cleaned and the particles removed therefrom aspirated through the main occlusion balloon catheter 12. As soon as the vessel has been thoroughly cleaned of plaque, the basket-like structure 103 can be moved from an expanded position to a collapsed position by movement of the slider 51 after which the basket-like structure 103 can be withdrawn into the distal extremity of the main occlusion balloon catheter 12. Thereafter, irrigation and aspiration can be discontinued followed by deflation of the balloons 79 and 21, after which the entire apparatus 101 can be removed from the vessel in a manner similar to that hereinbefore described.

Another apparatus 121 incorporating the present invention is shown in FIG. 5 in which the main occlusion balloon catheter 12 and the distal occlusion balloon catheter 13 are identical. A different therapeutic catheter 122 is provided. In place of the basket-like structure 103 provided on therapeutic catheter 102 and the helical coil 56 provided on the therapeutic catheter 14, a brush 123 is formed on the distal extremity 38 of the flexible elongate tubular member 36. The brush 123 is comprised of a plurality of radially extending bristles 124 formed of a suitable soft material such as Nylon with the brush 123 having an outer diameter corresponding generally to the inner diameter of the lumen 63 defined by the wall 62. The distal extremity 38 is provided with a plurality of randomly disposed ports 126 interposed between the bristles 124 for supplying irrigation liquid to the brush 123. The therapeutic catheter 122 can be deployed in a manner similar that hereinbefore described. With the balloons 79 and 21 inflated and with irrigation liquid being supplied through the ports 126 and aspiration taking place through the aspiration port 28, the brush 123 can be rotated by rotating the proximal extremity of the therapeutic catheter 122. By moving the catheter 122 back and forth, the bristles 124 can come into engagement with the wall 62 throughout the entire length of the chamber 91 to remove the plaque 64 in small particles. As the small particles are removed they can be aspirated from the chamber 91 through the aspiration port 28. It can be seen that in this embodiment of the therapeutic catheter, the use of a pull wire has been eliminated. After the cleaning procedure has been accomplished, the brush 123 can be retracted into the distal extremity 18 of the flexible elongate tubular member 16 of the main occlusion balloon catheter 12. After termination of irrigation and aspiration, the balloons 79 and 21 can be deflated and the entire assembly of apparatus 121 can be removed from the vessel and thereafter the puncture sealed.

It is apparent from the foregoing that there has been provided an apparatus and method for cleaning diseased vein grafts making possible additional years of life for the patient. The method and procedure can be accomplished rapidly without the need for perfusion of blood during the procedure. The apparatus can be readily used without the occurrence of downstream embolic events because of the closed chamber provided between the two occlusion balloons. Since the plaque being removed is relatively soft, it can readily and quickly removed. Although the apparatus and method of the present invention have been described principally in connection with the treatment of diseased vein grafts, it should be appreciated that the present apparatus and method can be utilized on other types of vessels. For example, such an apparatus and method can be utilized in vessels that have thrombus such as that which may occur in the carotids.

What is claimed is:

1. Apparatus for cleaning a vessel having a stenosis therein comprising first and second balloon catheters and having balloons disposed on opposite sides of the stenosis in the vessel and forming a closed chamber in the vessel and having proximal and distal extremities, a therapeutic catheter having a distal extremity disposed in the chamber end having lumen extending into the distal extremity and having a plurality of ports in the distal extremity in communication with said lumen, means coupled to the lumen in the therapeutic catheter for supplying an irrigation liquid to the chamber from the ports in the distal extremity of the therapeutic catheter as jets of irrigation liquid directed towards the proximal extremity of the chamber and means for aspirating irrigation liquid from the proximal extremity of the chamber to form an aspirate and means for causing movement of the distal extremity of the therapeutic catheter to cause the material forming the stenosis to be removed from the wall of the vessel and broken into particles and to be engaged by the jets of irrigation liquid and removed from the chamber with the aspirate.

2. Apparatus for cleaning a vessel having a stenosis therein comprising first and second balloon catheters and having balloons disposed on opposite sides of the stenosis in the vessel and forming a closed chamber in the vessel, a therapeutic catheter having a distal extremity disposed in the chamber, means for supplying an irrigation liquid to the chamber and means for aspirating irrigation liquid from the chamber to form an aspirate and removal means carried by the distal extremity of the therapeutic catheter for causing the material forming the stenosis to be removed from the wall of the vessel and broken into particles to be removed therefrom in the aspirate, said removal means carried by the distal extremity of the therapeutic catheter including a helical coil disposed over the distal extremity of the therapeutic catheter and movable between expanded and contracted positions while disposed over the distal extremity of the therapeutic catheter, said therapeutic catheter having a proximal extremity and having a handle secured to the proximal extremity, said handle including means for causing movement of said helical coil between expanded and contracted positions and permitting rotation of the therapeutic catheter by rotation of the handle.

3. Apparatus for cleaning a vessel having a stenosis therein comprising first and second balloon catheters and having balloons disposed on opposite sides of the stenosis in the vessel and forming a closed chamber in the vessel, a therapeutic catheter having a distal extremity disposed in the chamber, means for supplying an irrigation liquid to the chamber and means for aspirating irrigation liquid from the chamber to form an aspirate, removal means carried by the distal extremity of the therapeutic catheter and means for causing movement of the distal extremity of the therapeutic catheter to cause the material forming the stenosis to be removed from the wall of the vessel and broken into particles to be removed therefrom in the aspirate, said removal means carried by the distal extremity of the therapeutic catheter including a basket-like structure overlying the distal extremity of the therapeutic catheter and having a plurality of circumferentially spaced-apart longitudinally extending arms, said arms being movable between a contracted position in close proximity to the distal extremity of the therapeutic catheter and to an expanded position in engagement with the wall of the vessel and handle means carried by the therapeutic catheter for causing movement of the arms between contracted and expanded positions and permitting rotational movement of the therapeutic catheter by rotation of the handle means.

4. Apparatus for cleaning a vessel having a stenosis therein comprising first and second balloon catheters and having balloons disposed on opposite sides of the stenosis in the vessel and forming a closed chamber in the vessel having proximal and distal extremities, a therapeutic catheter having a distal extremity disposed in the chamber and having a lumen extending into the distal extremity and having a plurality of ports in the distal extremity in communication with said lumen, means coupled to the lumen in the therapeutic catheter for supplying an irrigation liquid to the chamber from the ports in the distal extremity of the therapeutic catheter as jets of irrigation liquid directed towards the proximal extremities of the chamber and means for aspirating irrigation liquid from the proximal extremity of the chamber to form an aspirate and means for causing movement of the distal extremity of the therapeutic catheter to cause the material forming the stenosis to be removed from the wall of the vessel and broken into particles and to be engaged by the jets of irrigation liquid and removed from the chamber with the aspirate, said means carried by the distal extremity of the therapeutic catheter including a brush having a plurality of radially extending bristles adapted to engage the wall of the vessel forming the vessel and handle means carried by the proximal extremity of the therapeutic catheter for causing rotational movement and back and forth movement of the brush in the vessel, said ports being disposed between the bristles so that the jets of the irrigation liquid pass through the bristles.

5. A method for cleaning a diseased vessel having a stenosis therein using first and second balloon occlusion catheters and a therapeutic catheter having a distal extremity with a plurality of ports therein, comprising advancing the first and second balloon occlusion catheters into the vessel so that the balloons are disposed on opposite sides of the stenosis, inflating the balloons to form a chamber having proximal and distal extremities between the balloons, advancing the therapeutic catheter into the chamber and causing movement of the distal extremity of the therapeutic catheter to remove material from the wall carrying the stenosis to form particles in the chamber, introducing an irrigation liquid through the therapeutic catheter as jets of irrigation liquid from the plurailty of ports in the distal extremity of the therapeutic catheter into the chamber in a direction toward the proximal extremity of the chamber and aspirating the irrigation liquid from the proximal extremity of the chamber and taking with it particles removed from the wall and continuing this procedure until the wall has been cleaned and the stenosis removed.

6. Apparatus as in claim 2 wherein said helical coil is formed of a shape memory alloy in an expanded position having an outer diameter corresponding to the inner diameter of the vessel.

* * * * *